(12) United States Patent
Gong et al.

(10) Patent No.: US 10,668,445 B2
(45) Date of Patent: Jun. 2, 2020

(54) UREA PREPARATION MACHINE (71) Applicants: ZHUHAI GREE INTELLIGENT EQUIPMENT CO., LTD., Guangdong (CN); GREE ELECTRIC APPLIANCES, INC. OF ZHUHAI, Guangdong (CN)

(72) Inventors: Ke Gong, Guangdong (CN); Xiufeng Zhang, Guangdong (CN)

(73) Assignees: Zhuhai Gree Intelligent Equipment Co., Ltd., Guangdong (CN); Gree Electric Appliances, Inc. of Zhuhai, Guangdong (CN)

( * ) Notice: Subject to any disclaimer, the term of this patent is extended or adjusted under 35 U.S.C. 154(b) by 53 days.

(21) Appl. No.: 16/304,267

(22) PCT Filed: Nov. 28, 2017

(86) PCT No.: PCT/CN2017/113338
§ 371 (c)(1),
(2) Date: Nov. 23, 2018

(87) PCT Pub. No.: WO2018/107961
PCT Pub. Date: Jun. 21, 2018

(65) Prior Publication Data
US 2019/0083952 A1 Mar. 21, 2019

(30) Foreign Application Priority Data
Dec. 13, 2016 (CN) .......................... 2016 1 1152567

(51) Int. Cl.
C07C 273/16 (2006.01)
C07C 273/02 (2006.01)
(Continued)

(52) U.S. Cl.
CPC .......... *B01J 19/0066* (2013.01); *B01D 15/10* (2013.01); *B01F 1/0038* (2013.01);
(Continued)

(58) Field of Classification Search
CPC .... B01J 19/0066; B01J 19/0013; B01J 19/18; B01F 1/0038; B01F 15/00974;
(Continued)

(56) References Cited

U.S. PATENT DOCUMENTS 4,009,048 A * 2/1977 Jensen ...................... B08B 3/08
134/12

FOREIGN PATENT DOCUMENTS

CN 105536635 5/2016
CN 105569784 5/2016
(Continued)

OTHER PUBLICATIONS

International Search Report corresponding to International Patent Application No. PCT/CN2017/113338, dated Feb. 24, 2018.

*Primary Examiner* — Madeline Gonzalez
(74) *Attorney, Agent, or Firm* — McAndrews, Held & Malloy, Ltd.

(57) ABSTRACT

A urea preparation machine includes a cabinet, a stirring tank, a filtering portion, a water tank portion and a heating portion. The stirring tank is provided in the cabinet. The filtering portion is provided in the cabinet. An inlet of the water tank portion is communicated with an outlet of the filtering portion. The heating portion is provided in the cabinet, the heating portion is communicated with the outlet of the water tank portion, and an outlet of the heating portion is communicated with the stirring tank. The independent heating portion is used for heating water in the water tank portion, then the water heated by the heating portion is conveyed to the stirring tank for preparing urea, through (Continued)

such installation, the heating portion is capable of heating the water in the water tank portion in time.

19 Claims, 6 Drawing Sheets

(51) Int. Cl.
*B01D 15/10* (2006.01)
*C02F 1/28* (2006.01)
*B01J 19/00* (2006.01)
*B01J 19/18* (2006.01)
*B01F 1/00* (2006.01)
*B01F 15/00* (2006.01)
*C02F 101/30* (2006.01)
*C02F 101/20* (2006.01)

(52) U.S. Cl.
CPC ..... *B01F 15/00974* (2013.01); *B01J 19/0013* (2013.01); *B01J 19/18* (2013.01); *C02F 1/283* (2013.01); *C07C 273/02* (2013.01); *C07C 273/16* (2013.01); *B01F 2215/008* (2013.01); *C02F 2101/20* (2013.01); *C02F 2101/30* (2013.01)

(58) Field of Classification Search
CPC ................ B01F 2215/008; C02F 1/283; C02F 2101/20; C02F 2101/30; B01D 15/10; C07C 273/02; C07C 273/16
USPC .............. 210/184, 175, 186, 167.02, 167.04, 210/167.06, 167.31, 167.32, 171, 172.1, 210/178, 179, 181, 191, 194, 195.1, 219, 210/258, 260, 180, 188, 218, 416.1
See application file for complete search history.

(56) References Cited

FOREIGN PATENT DOCUMENTS

| | | |
|---|---|---|
| CN | 205528160 | 8/2016 |
| CN | 106582336 | 4/2017 |
| CN | 106582426 | 4/2017 |
| CN | 106731911 | 5/2017 |
| CN | 106732162 | 5/2017 |
| CN | 107042080 | 8/2017 |
| CN | 206366319 | 8/2017 |
| CN | 206366320 | 8/2017 |
| CN | 206366361 | 8/2017 |
| CN | 206366365 | 8/2017 |
| CN | 206366366 | 8/2017 |
| KR | 1020050006458 | 1/2005 |
| WO | 2010/084080 | 7/2010 |

* cited by examiner

UREA PREPARATION MACHINE

RELATED APPLICATIONS

This application is a 371 of International Patent Application No. PCT/CN2017/113338, filed Nov. 28, 2017, entitled "UREA PREPARATION MACHINE" which claims priority to Chinese Patent Application No. 201611152567.6, filed Dec. 13, 2016, both of which are incorporated herein by reference in their entirety.

TECHNICAL FIELD

The present disclosure relates to a technical field of urea processing equipment, in particular to a urea preparation machine.

BACKGROUND

A heating device in a urea preparation machine in the related art is generally installed in a stirring tank, or installed in an ultrapure water tank for heating water which enters the stirring tank in the urea preparation machine and preparing urea solution. Heating modes in the existing technology are limited, in the case of using a lot of the urea solution, the user requirements cannot be satisfied by using the heating modes in the related art, and the production efficiency of the urea solution is reduced.

SUMMARY

Some embodiments of the present disclosure mainly aim to provide a urea preparation machine, and solve a problem in the related art that the production efficiency of the urea preparation machine is low.

In order to achieve the above purpose, according to some embodiments of the present disclosure, a urea preparation machine is provided, including: a cabinet; a stirring tank, provided in the cabinet; a filtering portion, provided in the cabinet; a water tank portion, wherein an inlet of the water tank portion is communicated with an outlet of the filtering portion; and a heating portion, provided in the cabinet, wherein the heating portion is communicated with an outlet of the water tank portion, and an outlet of the heating portion is communicated with the stirring tank.

In an exemplary embodiment, the heating portion is provided at one side of at least one of the stirring tank, the filtering portion and the water tank portion.

In an exemplary embodiment, the heating portion is provided at one side of the stirring tank, the filtering portion and the water tank portion.

In an exemplary embodiment, the filtering portion includes a filter, wherein the filter is provided at a bottom of the cabinet, a water inlet of the filter is communicated with an external water source, and a water outlet of the filter is communicated with the water tank portion.

In an exemplary embodiment, the filter includes: a candle filter, wherein a water inlet of the candle filter is communicated with the external water source, and a water outlet of the candle filter is communicated with the water tank portion.

In an exemplary embodiment, the filter further includes: an active carbon filter, wherein a water inlet of the active carbon filter is communicated with the water outlet of the candle filter, and a water outlet of the active carbon filter is communicated with the water tank portion.

In an exemplary embodiment, the filtering portion further includes: a first water pump, provided on a pipe between the stirring tank and the water tank portion.

In an exemplary embodiment, the filtering portion includes: a film filtering portion, wherein the film filtering portion is provided on a pipe between the stirring tank and the water tank portion and positioned above the first water pump.

In an exemplary embodiment, the water tank portion includes: a middle water tank, provided above the stirring tank, wherein a water inlet of the middle water tank is communicated with the water outlet of the filtering portion, and a water outlet of the middle water tank is communicated with the heating portion.

In an exemplary embodiment, the water tank portion further includes: a pure water tank, provided above the filtering portion and provided parallel to the middle water tank, wherein a water inlet of the pure water tank is communicated with the water outlet of the middle water tank, and a water outlet of the pure water tank is communicated with the heating portion.

In an exemplary embodiment, the filtering portion includes: a second water pump, provided on a bottom of the cabinet, wherein the second water pump is provided on a pipe connected between the middle water tank and the stirring tank.

In an exemplary embodiment, the urea preparation machine includes: a material absorbing device, wherein the material absorbing device is provided with a material absorbing port and a discharge port, the discharge port is communicated with a stirring cavity of the stirring tank, and the material absorbing port is used for absorbing urea and conveying the urea to the stirring cavity.

In an exemplary embodiment, the material absorbing device includes: a housing, wherein a first end of the housing is provided with a feed port, a second end of the housing is provided with a discharge port, the housing is further provided with an exhaust port, the exhaust port is used for exhausting air in the housing, and the feed port forms the material absorbing port.

In an exemplary embodiment, the material absorbing device further includes: a separating plate, wherein the separating plate is provided in the housing, an air inlet passage and an air exhaust passage are respectively formed between the separating plate and a side wall of the housing, the exhaust port is communicated with the air exhaust passage, and a flow passing port communicated with the air inlet passage and the air exhaust passage is formed between a bottom of the separating plate and the side wall of the housing.

In an exemplary embodiment, the separating plate includes: a first plate section, wherein the first plate section is provided along a vertical direction, a first end of the first plate section is connected with the housing, the feed port and the exhaust port are positioned at two opposite sides of the first plate section; and a second plate section, wherein the second plate section is connected with a second end of the first plate section and there is an included angle between the second plate section and the second end of the first plate section, and the second plate section is provided away from the exhaust port.

In an exemplary embodiment, the included angle between the second plate section and the second end of the first plate section is a right angle.

In an exemplary embodiment, the material absorbing device includes: a suction portion, wherein the suction portion is provided with a suction port and an export, the export is communicated with the feed port, and the suction port forms the material absorbing port.

In an exemplary embodiment, there are a plurality of material absorbing devices, the discharge port of the plurality of the material absorbing devices is communicated with the cavity of the stirring tank, a feed port of one material absorbing device in two neighboring material absorbing devices is communicated with an exhaust port of the other material absorbing device in the two neighboring material absorbing devices.

In an exemplary embodiment, the heating portion includes a heating water tank, wherein the heating water tank is used for storing and heating water from the water tank portion.

Applying the technical scheme of the present disclosure, the urea preparation machine includes a cabinet, a stirring tank, a filtering portion, a water tank portion and a heating portion. The stirring tank is provided in the cabinet. The filtering portion is provided in the cabinet. The inlet of the water tank portion is communicated with the outlet of the filtering portion. The heating portion is provided in the cabinet, the heating portion is communicated with the outlet of the water tank portion, the outlet of the heating portion is communicated with the stirring tank. The independent heating portion is used for heating water in the water tank portion, then the water heated by the heating portion is conveyed to the stirring tank for preparing urea, through such installation, the heating portion is capable of heating the water in the water tank portion in time, the efficiency of the urea preparation machine is effectively improved, and the user requirements are satisfied.

BRIEF DESCRIPTION OF THE DRAWINGS

The accompanying drawings, which constitute a part of this application, are used to provide a further understanding of the present disclosure, and the exemplary embodiments of the present disclosure and the description thereof are used to explain the present disclosure, but do not constitute improper limitations to the present disclosure. In the drawings.

The above drawings include the following drawing marks:
10: cabinet;
20: stirring tank;
21: material absorbing device;
211: feed port; 212: exhaust port; 213: separating plate; 214: water inlet;
2131: first plate section; 2132: second plate section;
22: suction portion;
23: beating portion; 231: connecting rod; 232: rolling plate; 233: handle; 234: striker plate;
30: filtering portion;
31: candle filter; 32: active carbon filter; 33: first water pump; 34: film filtering portion; 35: second water pump;
40: water tank portion; 41: middle water tank; 42: pure water tank; 43: liquid storage tank;
50: heating portion;
60: feed pipe section;
70: temperature control portion; 71: refrigerating device; 72: heating device.

DETAILED DESCRIPTION OF THE EMBODIMENTS

It is to be noted that the embodiments in the present disclosure and the features in the embodiments may be mutually combined in the case without conflicting. The present disclosure is explained in detail with reference to the drawings in combination with the embodiments below.

It is to be noted that terms used herein only aim to describe specific implementation manners, and are not intended to limit exemplar implementations of this application. Unless otherwise directed by the context, singular forms of terms used herein are intended to include plural forms. Besides, it will be also appreciated that when terms "contain" and/or "include" are used in the description, it is indicated that features, steps, operations, devices, assemblies and/or a combination thereof exist.

It is to be noted that the specification and claims of the disclosure and terms 'first', 'second' and the like in the drawings are intended to distinguish similar objects, and are not necessarily to describe a specific sequence or a precedence order. It is to be understood that terms used in such a way may be exchanged under appropriate conditions, in order that the embodiments of the disclosure described here can be implemented in a sequence except sequences graphically shown or described here. In addition, terms 'comprise', 'include' and variations thereof are intended to cover non-exclusive inclusions. For example, processes, methods, systems, products or devices containing a series of steps or units do not need to clearly show those steps or units, and may include other inherent steps or units of these processes, methods, products or devices, which are not clearly shown.

For ease of description, spatial relative terms such as "over", "above", "on an upper surface" and "upper" may be used herein for describing a spatial position relation between a device or feature and other devices or features shown in the drawings. It will be appreciated that the spatial relative terms aim to contain different orientations in usage or operation besides the orientations of the devices described in the drawings. For example, if the devices in the drawings are inverted, devices described as "above other devices or structures" or "over other devices or structures" will be located as "below other devices or structures" or "under other devices or structures". Thus, an exemplar term "above" may include two orientations namely "above" and "below". The device may be located in other different modes (rotated by 90 degrees or located in other orientations), and spatial relative descriptions used herein are correspondingly explained.

Now, the exemplary embodiments according to the present disclosure are described in detail with reference to the drawings. However, the example embodiments may be implemented in multiple different modes, and are not intended to be limited by the described implementation modes herein. It is to be understood that the implementation modes are provided so that the present disclosure is completely and totally disclosed, and the conceptions of the example implementation modes are adequately transmitted to those of ordinarily skill in the art, in the drawings, for clarity, the thicknesses of layers and areas may be enlarged, and the same drawing mark is used for representing the same device, so that their description is omitted.

The urea solution production device in the existing technology mainly includes three types, one type is large-scale chemical equipment, generally used for a professional large-scale urea solution manufacturer, one type is a small-scale device in low integration level, such device is generally formed by more than three parts, which need to be spliced on site frequently, so that great difficulty is brought to the installation and debugging of the device. Another type is a urea solution production device in high integration level. The device is integrated with multiple modules of water purification, air energy heating, stirring, solution storage, feeding and the like. Although the device has a higher integration level, the volume of the device is larger, the transportation is inconvenient, the internal pipeline arrangement of the device is complicated and the batch production is inconvenient.

In combination with FIG. 1 to FIG. 8, according to the embodiments of the present disclosure, a urea preparation machine is provided.

Figure 5:
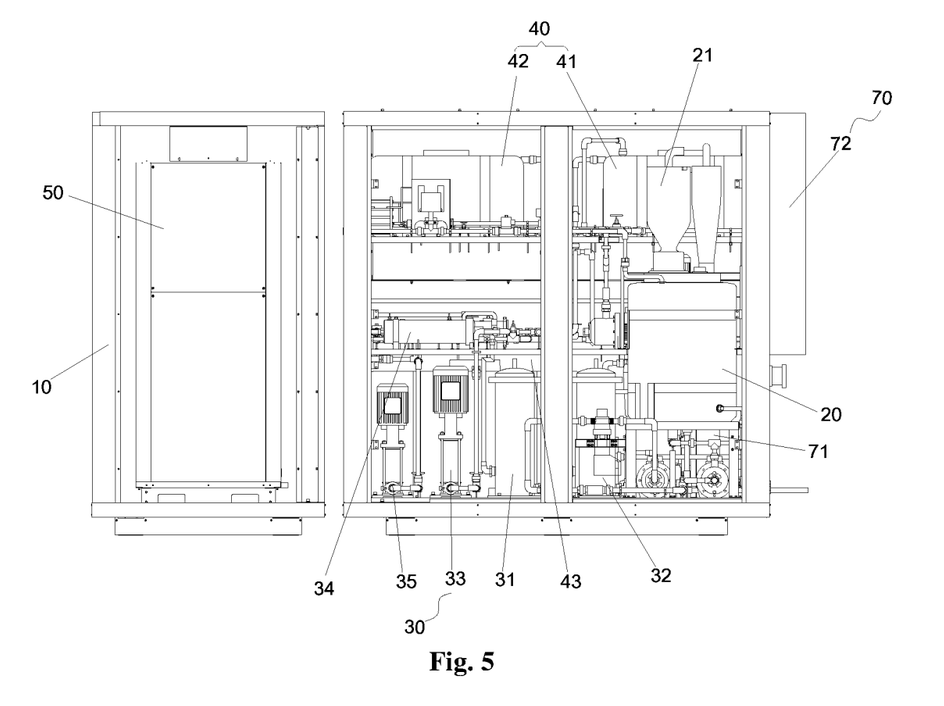
FIG. 5 shows a structure schematic diagram of the urea preparation machine in FIG. 1.
Figure 6:
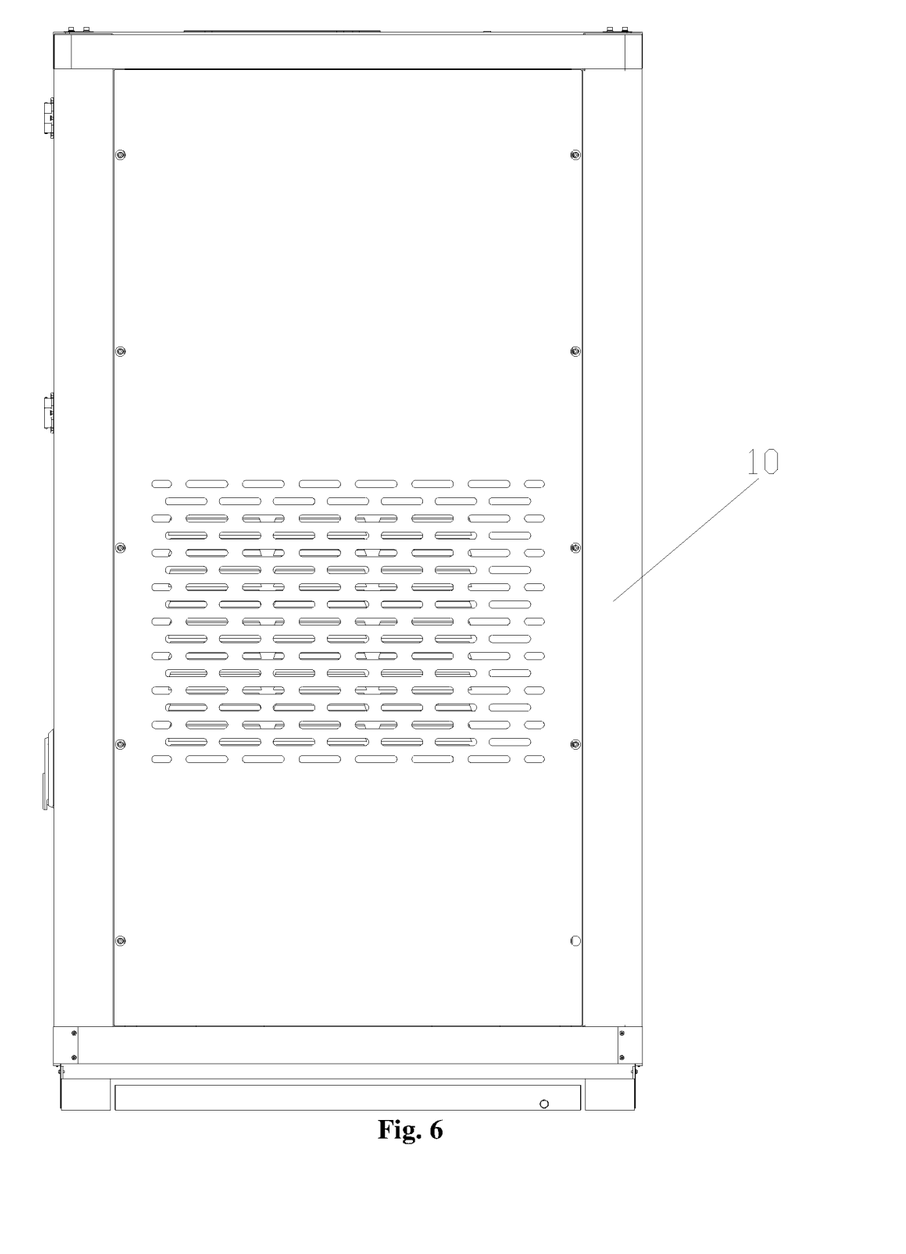
FIG. 6 shows a structure schematic diagram of the first perspective of the urea preparation machine in FIG. 5.
Figure 7:
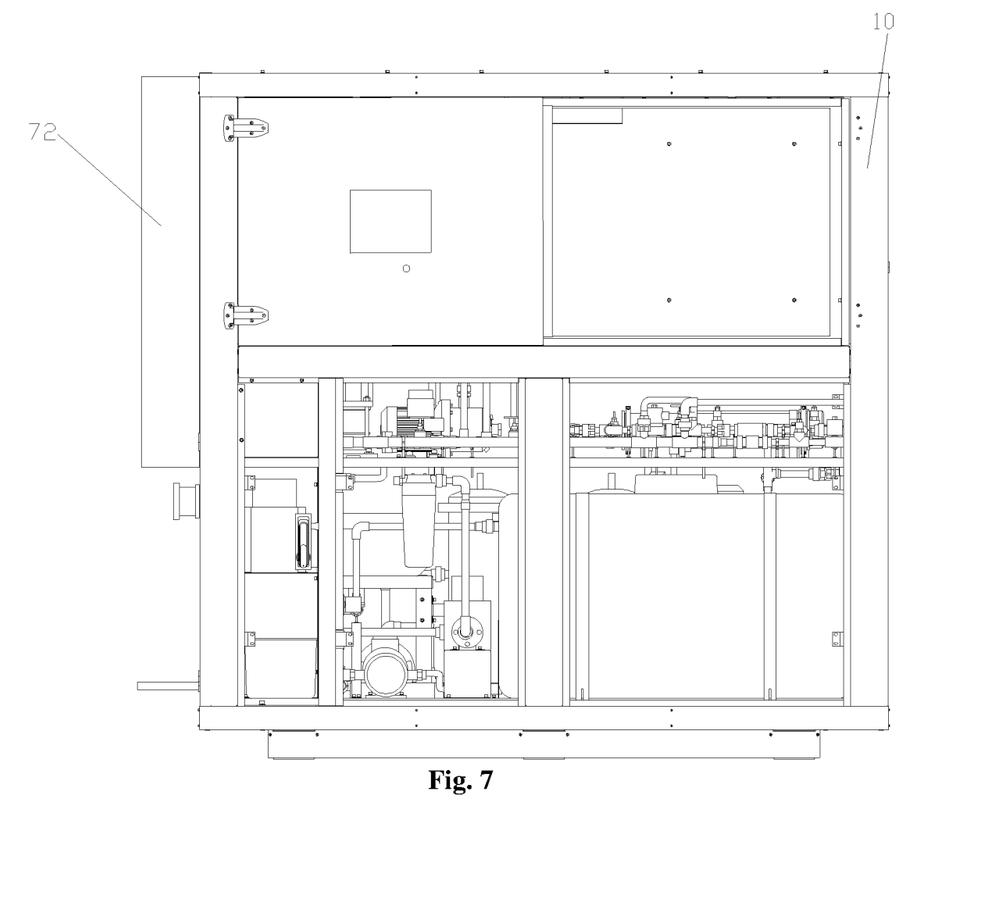
FIG. 7 shows a structure schematic diagram of the second perspective of the urea preparation machine in FIG. 5.
Figure 8:
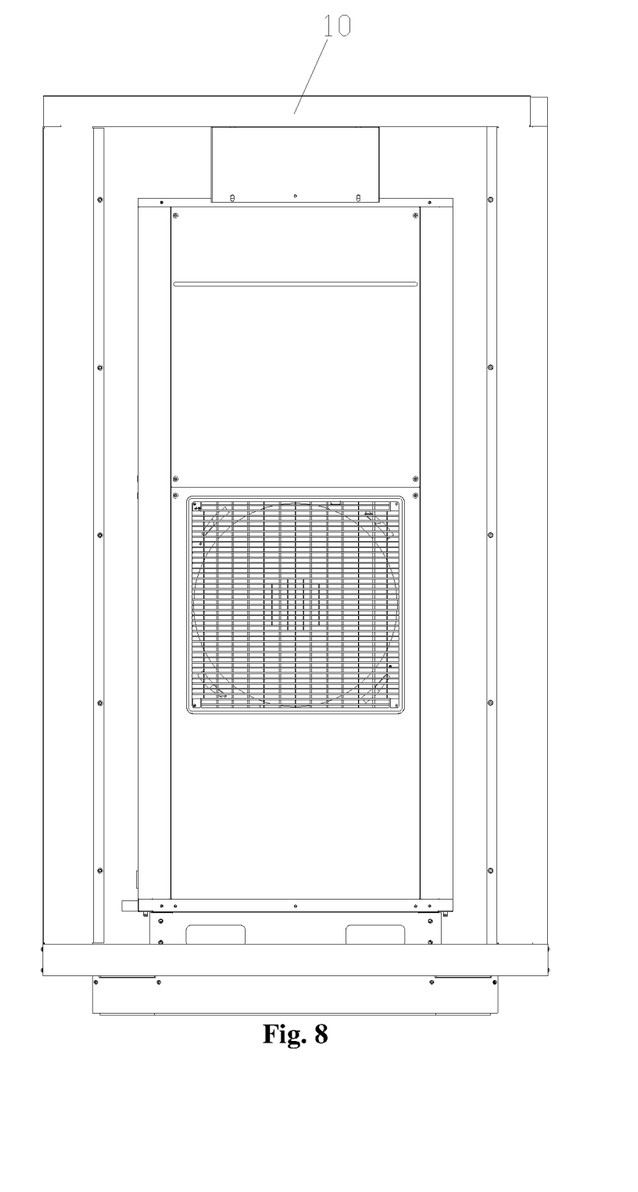
FIG. 8 shows a structure schematic diagram of the third perspective of the urea preparation machine in FIG. 5.

In an exemplary embodiment, the urea preparation machine includes a cabinet 10, a stirring tank 20, a filtering portion 30, a water tank portion 40 and a heating portion 50. The stirring tank 20 is provided in the cabinet 10. The filtering portion 30 is provided in the cabinet 10. An inlet of the water tank portion 40 is communicated with an outlet of the filtering portion 30. The heating portion 50 is provided in the cabinet 10, the heating portion 50 is communicated with an outlet of the water tank portion 40, and an outlet of the heating portion 50 is communicated with the stirring tank 20.

In the embodiment, the independent heating portion 50 is used for heating water in the water tank portion 40, then the water heated by the heating portion 50 is conveyed to the stirring tank 20 for preparing urea, through such installation, the heating portion 50 is capable of heating the water in the water tank portion 40 in time, the efficiency of the urea preparation machine is effectively improved, and the user requirements are satisfied.

The heating portion 50 is provided at one side of at least one of the stirring tank 20, the filtering portion 30 and the water tank portion 40. Such installation is capable of effectively reducing the processing difficulty of a housing of the urea preparation machine, and enabling the arrangement of the urea preparation machine to be more rational and simple. In an exemplary embodiment, as shown in FIG. 5, the heating portion 50 is provided at one side of the stirring tank 20, the filtering portion 30 and the water tank portion 40.

The filtering portion 30 includes a filter. The filter is provided at a bottom of the cabinet 10, a water inlet of the filter is communicated with an external water source, and a water outlet of the filter is communicated with the water tank portion 40. Such installation is capable of effectively filtering impurities from the external water source, and effectively improving the quality of the urea solution.

In an exemplary embodiment, the filter includes a candle filter 31. A water inlet of the candle filter 31 is communicated with an external water source, and a water outlet of the candle filter 31 is communicated with the water tank portion 40. Such installation is capable of effectively filtering small particles of fine sand and other impurities in the water source.

In an exemplary embodiment, in order to further improve the filtering performance of the filter, the filter includes an active carbon filter 32. A water inlet of the active carbon filter 32 is communicated with the water outlet of the candle filter 31, and a water outlet of the active carbon filter 32 is communicated with the water tank portion 40. Such installation is capable of effectively removing low-molecular weight organic matters and heavy metals in water from the candle filter 31.

In order to guarantee that the whole water cycle has an enough water pressure, in an exemplary embodiment, the filtering portion 30 includes a first water pump 33. The first water pump 33 is provided on a pipe between the stirring tank 20 and the water tank portion 40.

In an exemplary embodiment, the filtering portion 30 includes a film filtering portion 34. The film filtering portion 34 is provided on a pipe between the stirring tank 20 and the water tank portion 40 and positioned above the first water pump 33. Such installation may further enable the filtering function to the external water source, effectively improve the water quality, thereby improve the urea solution quality, and increase the reliability of the urea preparation machine.

In an exemplary embodiment, the water tank portion 40 includes a middle water tank 41. The middle water tank 41 is provided above the stirring tank 20, a water inlet of the middle water tank 41 is communicated with a water outlet of the filtering portion 30, and a water outlet of the middle water tank 41 is communicated with the heating portion 50. Such installation is capable of storing the filtered water in the middle water tank, and storing enough water source for future use while the urea solution needs to be produced in batches.

In an exemplary embodiment, the water tank portion 40 includes a pure water tank 42. The pure water tank is provided above the filtering portion 30 and provided parallel to the middle water tank 41, a water inlet of the pure water tank 42 is communicated with the water outlet of the middle water tank 41, and a water outlet of the pure water tank 42 is communicated with the heating portion 50. Such installation is capable of preparing pure water by using water in the middle water tank 41 while the pure water tank 42 prepares the pure water, and conveying to the heating portion 50 for heating. A rate of preparing urea by the urea preparation machine is effectively improved.

In an exemplary embodiment, the water tank portion 40 includes a liquid storage tank 43. The liquid storage tank 43 is provided at the bottom of the cabinet 10, a first water pump 33 is provided at one side of the liquid storage tank 43, a liquid inlet of the liquid storage tank 43 is communicated with a liquid outlet of the stirring tank 20, and a liquid outlet of the liquid storage tank 43 is communicated with the user end. The liquid storage tank 43 and the first water pump 33 are provided on the bottom of the cabinet 10, such installation is capable of avoiding a condition that the gravity of the urea preparation machine cabinet is higher and unstable caused by providing the first water pump 33 in heavier weight on the liquid storage tank 43. The liquid storage tank 43 provided in the bottom is used for storing the urea solution prepared in the stirring tank and for future use.

In an exemplary embodiment, the filtering portion 30 includes a second water pump 35. The second water pump 35 is provided on the bottom of the cabinet 10, the second water pump 35 is provided on a pipe connected between the middle water tank 41 and the stirring tank 20. Such installation is capable of effectively guaranteeing that enough water pressure is formed between the pipes so that the water flow transportation is performed.

As shown in FIG. 1 to FIG. 4, the urea preparation machine includes a material absorbing device 21. The material absorbing device 21 is provided with a material absorbing port and a discharge port, the discharge port is communicated with a stirring cavity of the stirring tank 20, and the material absorbing port is used for absorbing urea and conveying the urea to the stirring cavity. The material absorbing device is used for feeding urea particles, effectively increasing the stability and reliability of feeding the urea particles.

Figure 1:
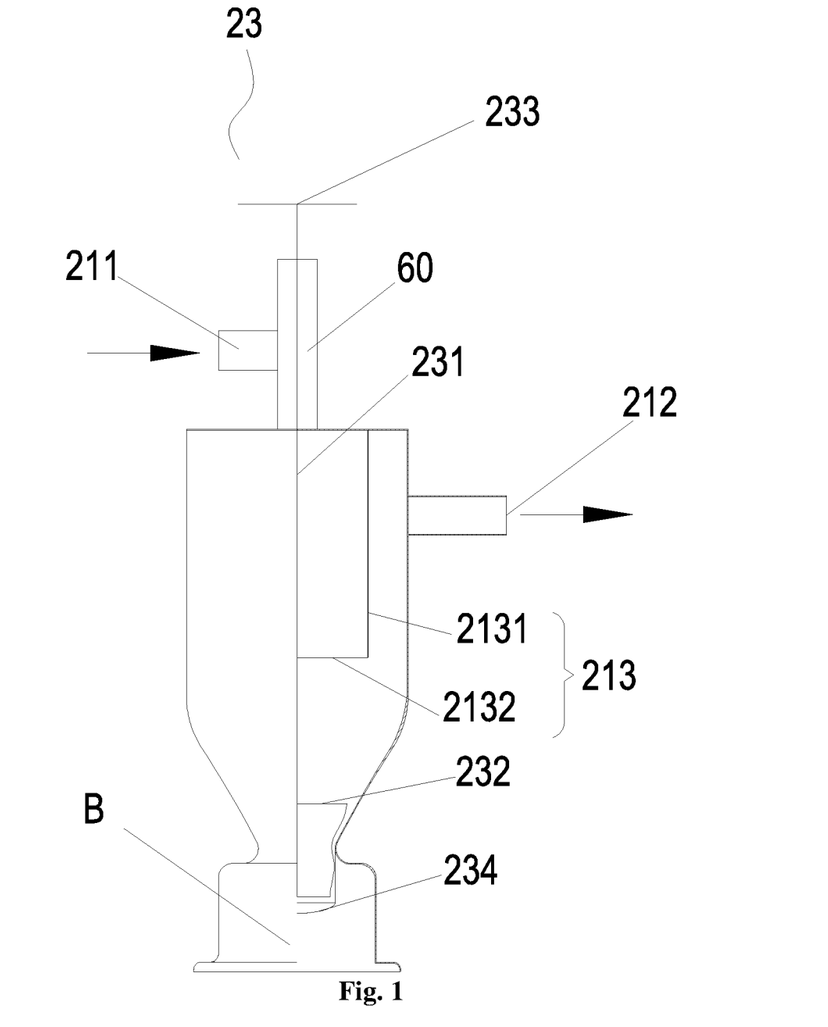
FIG. 1 shows a structure schematic diagram of a first embodiment according to the material absorbing device of the urea preparation machine of the present disclosure.
Figure 2:
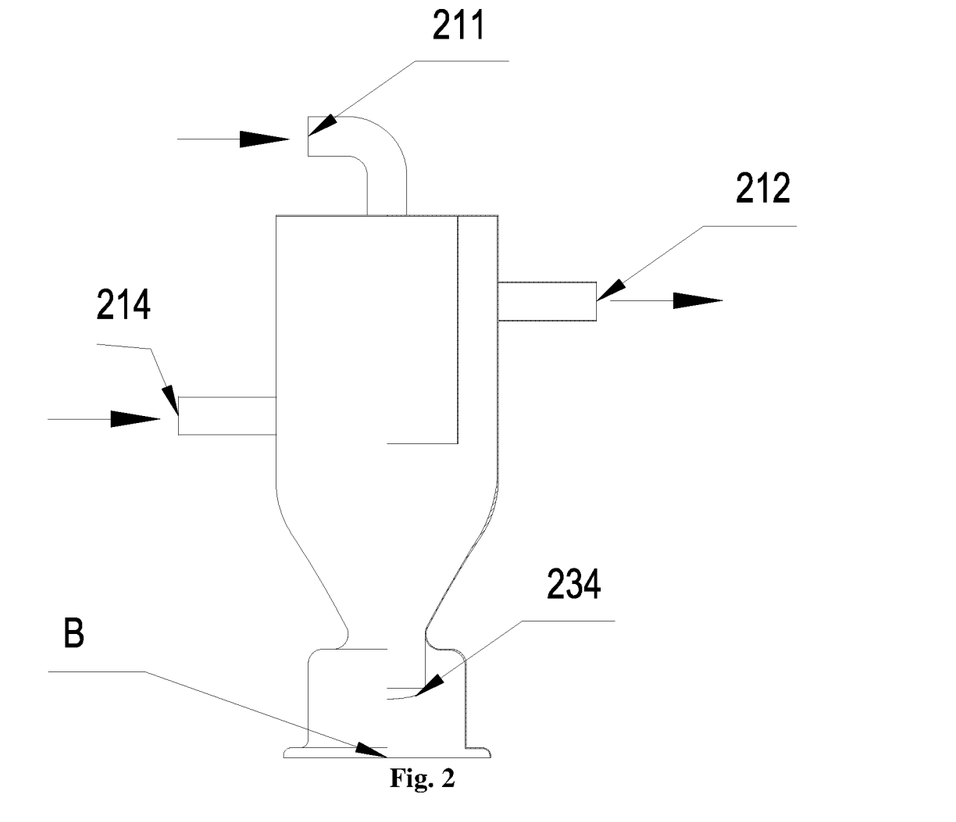
FIG. 2 shows a structure schematic diagram of a second embodiment of the material absorbing device of the urea preparation machine in FIG. 1.

Wherein, the material absorbing device 21 includes a housing. A first end of the housing is provided with a feed port 211, a second end of the housing is provided with the discharge port, the housing is further provided with an exhaust port 212, the exhaust port 212 is used for exhausting air in the housing, and the feed port 211 forms the material absorbing port. Such installation is capable of effectively increasing the stability and reliability of feeding the urea particles.

In an exemplary embodiment, the material absorbing device 21 includes a separating plate 213. The separating plate 213 is provided in the housing, an air inlet passage and an air exhaust passage are respectively formed between the separating plate 213 and a side wall of the housing, the exhaust port 212 is communicated with the air exhaust passage, and a flow passing port communicated with the air inlet passage and the air exhaust passage is formed between a bottom of the separating plate 213 and the side wall of the housing. By such installation, the urea particles is conveyed into the air inlet passage in the housing through a pipe and conveyed to the stirring tank for urea preparation through the discharge port, and the arrangement is capable of preventing an exhaust adsorption force in the exhaust port from affecting the urea particles entering the housing so that the urea particles are discharged through the exhaust port, the urea particles are wasted and the urea production cost is increased. The economic benefit of the urea preparation machine is effectively improved.

In an exemplary embodiment, the separating plate 213 includes a first plate section 2131 and a second plate section 2132. The first plate section 2131 is provided along a vertical direction, a first end of the first plate section 2131 is connected with the housing, and the feed port 211 and the exhaust port 212 are provided at both opposite sides of the first plate section 2131. The second plate section 2132 is connected with a second end of the first plate section 2131 and has an included angle, the second plate section 2132 is provided away from the exhaust port 212. Such installation is capable of effectively preventing the urea particles from blocking the feed port, and preventing the urea particles from being discharged so as to cause the resource waste.

In an exemplary embodiment, the second plate section 2132 is connected with the second end of the first plate section 2131 and has an included angle, and the included angle is a right angle. Such installation is capable of effectively preventing the urea particles from being discharged so as to cause the waste. In addition, the included angle is set as a right angle, a speed of the urea particles falling into the stirring tank may be effectively buffered, and a problem that a lot of the particles are stacked in the feed port of the material absorbing device at the same time, thereby causing blocking of the feed port is avoided.

Figure 3:
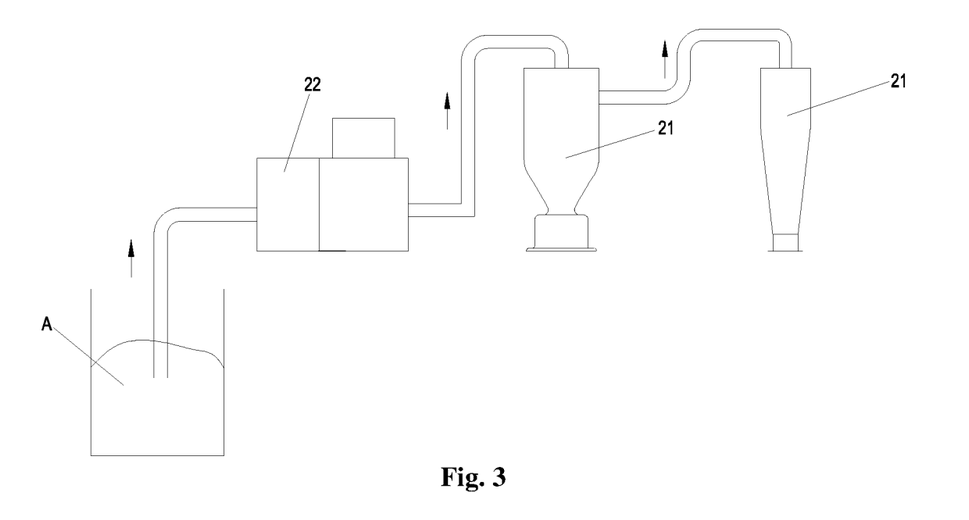
FIG. 3 shows a structure flow diagram of a first embodiment of the material absorbing device of the urea preparation machine in FIG. 1.
Figure 4:
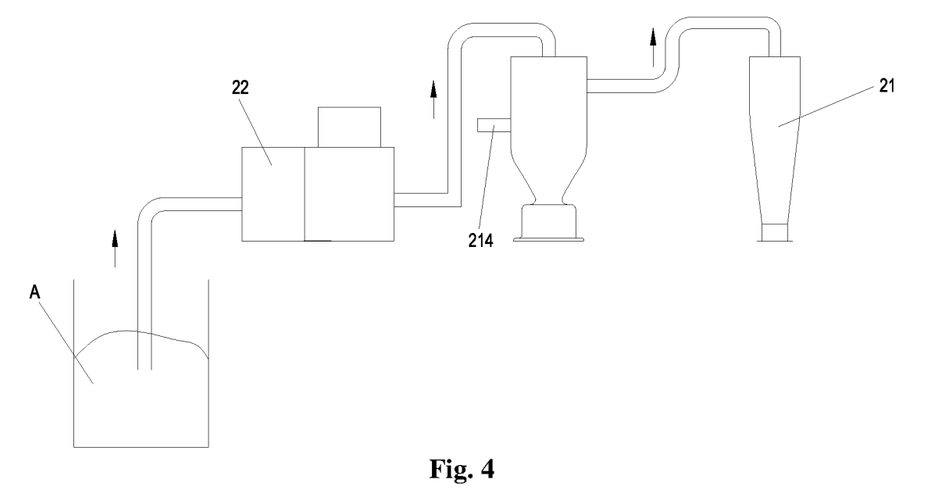
FIG. 4 shows a structure flow diagram of a second embodiment of the material absorbing device of the urea preparation machine in FIG. 2.

As shown in FIG. 3 and FIG. 4, in order to enable the urea particles to enter the stirring tank smoothly, the material absorbing device 21 includes a suction portion 22. The suction portion 22 is provided with a suction port and an export, the export is communicated with the feed port 211, and the suction port forms a material absorbing port. The suction port is positioned in a container loaded with the urea particles, and the export is communicated with the feed port, so that while a motor of the suction portion 22 is opened to be operated, the urea particles may be smoothly conveyed to the stirring tank.

In order to prevent a part of the urea particles from being discharged along the air exhaust passage, a plurality of material absorbing devices 21 are provided, the discharge port of each of the material absorbing devices 21 is communicated with a cavity of the stirring tank, the feed port 211 of one material absorbing device 21 in two neighboring material absorbing devices 21 is communicated with the exhaust port 212 of the other material absorbing device 21 in two neighboring material absorbing devices 21. Through such installation, while a part of the urea particles is discharged through the air exhaust passage of the previous material absorbing device, the part of the urea particles enters the next material absorbing device again, and is conveyed to the discharge port through an air inlet pipe in the material absorbing device and enters the stirring tank, a secondary air exhaust function is achieved. The same mode may be successively analogized. Such installation is capable of effectively and totally conveying the urea particles in a conveying pipe to the stirring tank for preparing the urea solution, and enabling a utilization ratio of the urea particles to be a hundred percent and zero waste.

In an exemplary embodiment, the heating portion 50 includes a heating water tank. The heating water tank is used for storing and heating water from the water tank portion 40. Such installation is capable of enabling the heating water tank to store water in a certain temperature, while the urea solution is prepared, the water in the water tank portion 40 is conveyed to the heating water tank for heating, as the originally stored water in the heating water tank has the quite high temperature, after the water from the water tank portion 40 is mixed with the original water, the water in the heating water tank may reach the needed water temperature after a short time of heating, and then the water is conveyed to the stirring tank for preparing the urea solution, the heating time of the needed water for preparing the urea solution may be effectively shortened, and the applicability and the reliability of the urea solution are improved.

The urea preparation machine uses a divided structure. The urea preparation machine device is divided into two parts of a main machine and an auxiliary machine, the main machine is integrated with ultrapure water filtering, ultrapure water storage, urea particle feeding, urea solution stirring, and urea solution storage, the auxiliary machine is an air energy water heater which is mainly responsible for heating ultrapure water. The main machine uses a three-layer arrangement structure, heavy and frequently maintained and adjusted materials of a water pump, a finished product solution storage tank, and a stirring tank and the like are provided on a bottom layer, frequently adjusted and maintained materials of a reverse osmosis (RO) reverse osmosis film, a water pipe, a magnetic valve and a water pump with light weight and the like are provided on a middle layer, materials with light weight of a middle water tank, an ultrapure water tank, and an electrodeionization (EDI) system and the like are provided on a top layer, so that the gravity of the main machine is reduced as possible, the device is convenient to transport, and the structure is stable. The materials which need to be frequently repaired, replaced and maintained and the like are provided on positions easy to repair, replace and maintain. The air energy water heater is used for heating, a heat pump principle is used for absorbing heat from a surrounding environment, the heat is transmitted to a condenser through a compressor, and released to water in the water tank, and the water is heated.

In an exemplary embodiment, the material absorbing device includes a beating portion 23. The beating portion 23 is rotatably provided in the housing so as to remove urea adhered to the housing. Such installation is capable of preventing the urea particles from being adhered to an inner wall of the housing so that a feeding speed of the urea particles is affected. Such installation is capable of guaranteeing the stability and the reliability of the feeding speed of the material absorbing device.

In an exemplary embodiment, the beating portion 23 includes a connecting rod 231 and a rolling plate 232. The connecting rod 231 is rotatably provided at the feed port 211, a first end of the connecting rod 231 is extended towards an interior of the housing, and a second end of the connecting rod 231 is extended towards an exterior of the housing. The rolling plate 232 is connected with the first end of the connecting rod 231, the rolling plate 232 is extended along the side wall of the housing, and the connecting rod 231 drives the rolling plate 232 to be rotated along a circumferential direction of the housing. In a rotation process, the rolling plate 232 may remove the urea particles adhered to the side wall of the housing, the urea particles are prevented from being accumulated on the inner wall of the housing so that the stability of feeding the urea particles is affected. In an exemplary embodiment, a tail end of the rolling plate 232 is configured to form a gap with the side wall of the housing.

In order that an operator conveniently removes the urea particles adhered to the inner wall, the second end of the connecting rod 231 is provided with a T-shaped handle 233. Through holding the handle 233 by a hand and rotating the handle 233, the beating function may be achieved.

In an exemplary embodiment, the beating portion 23 includes a striker plate 234. The striker plate 234 is provided in the housing and positioned below the rolling plate 232. The striker plate may be provided for reducing a speed of the urea particles entering the stirring tank, the buffering function is achieved, and the oversize and overquick urea particles are prevented from entering. In addition, the striker plate 234 may prevent the urea particles positioned below the striker plate 234 from being reversely absorbed into the above housing so that the urea particles are discharged out of the housing and the urea particles are wasted.

As shown in FIG. 2, in an exemplary embodiment, in order to clean the interior of the housing in time, the housing is provided with a water inlet 214. Water is conveyed into the housing through the water inlet 214, so that the interior of the housing is cleaned, the urea particles are prevented from being adhered to the inner wall of the housing for a long time, so the housing is corroded, and the service life of the housing is affected.

With reference to FIG. 1, in an exemplary embodiment, the material absorbing device includes a feed pipe section 60. One end of the feed pipe section 60 is communicated with the cavity of the housing, a side wall of the feed pipe section 60 is provided with the feed port 211, the other end of the feed pipe section 60 is a free end and closed, a part of the connecting rod 231 is positioned in the feed pipe section 60 and the connecting rod 231 and the feed pipe section 60 are provided coaxially. Such installation is capable of effectively installing the connecting rod 231 on the housing and realizing the rotation.

In an exemplary embodiment, the urea preparation machine includes a cabinet 10 and a temperature control portion 70. The temperature control portion 70 is provided in the cabinet 10, and the temperature control portion 70 is used for controlling the temperature in the cabinet 10 to be within a preset temperature range.

In the embodiment, the interior of the urea preparation machine cabinet is provided with the temperature control portion capable of effectively controlling the temperature in the cabinet to be within a certain range, thus effectively guaranteeing the temperature in the cabinet always to be within a constant temperature range, and guaranteeing the quality of the urea solution stored in the cabinet.

In an exemplary embodiment, the urea preparation machine includes a stirring tank 20 and a water tank portion 40. The stirring tank 20 and the water tank portion 40 are provided in the cabinet 10, the temperature control portion 70 is used for controlling the temperature of the urea solution in the water tank portion 40 to be within a preset temperature range. Such installation is capable of effectively keeping the temperature of the water tank provided in the cabinet 10 to be within a certain temperature range value always, and effectively improving the usability of the urea preparation machine and the reliability of preparing the urea solution.

In an exemplary embodiment, the water tank portion 40 includes a liquid storage tank 43. The liquid storage tank 43 is provided on the bottom of the cabinet 10, the liquid inlet of the liquid storage tank 43 is communicated with the liquid outlet of the stirring tank 20, the liquid outlet of the liquid storage tank 43 is communicated with a user end, and the temperature control portion 70 is used for controlling the temperature in the liquid storage tank 43, so that the temperature of the urea solution in the liquid storage tank 43 is positioned within a preset temperature range. Such installation is capable of effectively controlling the storage temperature of the urea solution in the liquid storage tank 43. In an exemplary embodiment, the preset temperature is marked as t, wherein t is greater than or equal to 5° C., and is less than or equal to 35° C. Namely, the internal temperature of the cabinet 10 is controlled within the range, the urea solution stored in the liquid storage tank 43 may be effectively prevented from being affected by the excessive high or excessive low temperature, so the quality of the urea solution is affected.

The temperature control portion 70 includes a refrigerating device 71. The refrigerating device 71 is provided above the cabinet 10 so as to reduce the temperature in the cabinet 10. In order to avoid the excessive high temperature in the cabinet, the cabinet 10 is provided with the refrigerating device 71 capable of reducing the internal temperature of the cabinet. The refrigerating device may be an evaporator, or a radiator, for example, a fan.

In order to prevent the temperature in the cabinet 10 is excessively low, in an exemplary embodiment, the temperature control portion 70 includes a heating device 72. The heating device 72 is provided in the cabinet 10, and the heating device 72 is used for increasing the temperature in the cabinet 10. Such installation is capable of effectively preventing the excessive low temperature of the urea solution in the liquid storage tank 43 so that urea is separated out and the urea solution is reduced. The reliability of the urea preparation machine for preparing the urea solution is effectively improved.

In an exemplary embodiment, the temperature control portion 70 includes a temperature sensor and a controller, the controller controls the temperature in the cabinet 10 according to a detection result of the temperature sensor. Such installation is capable of effectively increasing the controllability of the internal temperature of the cabinet. In addition, the intelligent control to the internal environment temperature of the cabinet 10 is improved, and the sensibility of the environment temperature control of the cabinet is improved.

In an exemplary embodiment, in order to improve the reliability of a temperature control system, a plurality of heating devices 72 may be provided in the cabinet. The heating device 72 may be an electric heating tube with a heating function or a heat exchange coil with an instant heating function.

In an exemplary embodiment, the cabinet 10 is provided with a door plate structure. The door plate structure is provided with a door plate body, and the door plate body is internally provided with a foam material. Such installation is capable of effectively guaranteeing the stability of the temperature in the cabinet 10, so that the cabinet 10 has a heat-insulating function.

In an exemplary embodiment, the foam material includes isocyanate and premixed polyether polyol. The door plate structure manufactured by using the isocyanate and premixed polyether polyol has a stronger heat-insulating effect.

In order to further improve the heat-insulating function of the door plate structure, and prevent air in the cabinet from performing the heat exchange with an external air through the door plate structure, an edge in the door plate body is provided with sponge and foam rubber. In at least one alternative embodiment, it may be one of the sponge and the foam rubber.

Adopting a divided structure, the urea preparation machine device is divided to two parts of a main machine and an auxiliary machine, the main machine is integrated with ultrapure water filtering, ultrapure water storage, urea particle feeding, urea solution stirring, and urea solution storage, and the auxiliary machine is an air energy water heater which is mainly responsible for heating ultrapure water.

The main machine uses a three-layer arrangement structure, heavy and frequently maintained and adjusted materials of a water pump, a finished product solution storage tank, and a stirring tank and the like are provided on a bottom layer, frequently adjusted and maintained materials of a RO reverse osmosis film, a water pipe, a magnetic valve and a water pump with light weight and the like are provided on a middle layer, materials with light weight of a middle water tank, an ultrapure water tank, and an EDI and the like are provided on a top layer, so the gravity of the main machine is reduced as possible, the device is convenient to transport, and the structure is stable.

The materials which need to be frequently repaired, replaced and maintained and the like are provided on positions easy to repair, replace and maintain.

The air energy water heater is used for heating, a heat pump principle is used for absorbing heat from a surrounding environment, the heat is transmitted to a condenser through a compressor, and released to water in the water tank, and the water is heated.

In an exemplary embodiment, ultrapure water is directly conveyed to an air energy water heater for heating to 35° C. or above. The air energy water heater is used for heating, a heat pump principle is used for absorbing heat from a surrounding environment, the heat is transmitted to a condenser through a compressor, and released to water in the water tank, and the water is heated, an energy exchange process is decreased, and the heating efficiency is improved. A water tank of the air energy water heater uses a mode of foam heat insulation, and the heat loss of the heated ultrapure water is avoided. In an exemplary embodiment, a working flow of the whole urea preparation machine including: water source, pre-processing (removing particle impurities), two-level reverse osmosis (preliminarily removing ions in water), EDI (further removing trace ions in water), ultrapure water, air energy water heater (heating water to 35° C. or more), stirring tank, and finished product tank.

The suction portion 22 absorbs the urea particles from a container (as shown in A of FIG. 3 and FIG. 4) loaded with the urea particles and conveys the urea particles to the material absorbing device 21 (two material absorbing devices 21 respectively as shown in FIG. 3 and FIG. 4), and conveys the urea particles to the urea stirring tank for preparing urea solution through the feed port (as shown in B of FIG. 1 and FIG. 2) of the material absorbing devices 21.

The above is only some embodiments of the present disclosure, not intended to limit the present disclosure. As will occur to those skilled in the art, the present disclosure is susceptible to various modifications and changes. Any modifications, equivalent replacements, improvements and the like made within the spirit and principle of the present disclosure shall fall within the scope of protection of the present disclosure.

What is claimed is:

1. A urea preparation machine, comprising:
   a cabinet;
   a stirring tank, provided in the cabinet;
   a filtering portion, provided in the cabinet;
   a water tank portion, wherein an inlet of the water tank portion is communicated with an outlet of the filtering portion;
   and a heating portion, provided in the cabinet, wherein the heating portion is communicated with an outlet of the water tank portion, and an outlet of the heating portion is communicated with the stirring tank;
   wherein the urea preparation machine comprises:
   a material absorbing device, wherein the material absorbing device is provided with a material absorbing port and a discharge port, the discharge port is communicated with a stirring cavity of the stirring tank, and the material absorbing port is used for absorbing urea and conveying the urea to the stirring cavity.

2. The urea preparation machine as claimed in claim 1, wherein the heating portion is provided at one side of at least one of the stirring tank, the filtering portion and the water tank portion.

3. The urea preparation machine as claimed in claim 2, wherein the heating portion is provided at one side of the stirring tank, the filtering portion and the water tank portion.

4. The urea preparation machine as claimed in claim 2, wherein the filtering portion comprises a filter, wherein the filter is provided at a bottom of the cabinet, a water inlet of the filter is communicated with an external water source, and a water outlet of the filter is communicated with the water tank portion.

5. The urea preparation machine as claimed in claim 4, wherein the filter comprises:
   a candle filter, wherein a water inlet of the candle filter is communicated with the external water source, and a water outlet of the candle filter is communicated with the water tank portion.

6. The urea preparation machine as claimed in claim 5, wherein the filter further comprises:
an active carbon filter, wherein a water inlet of the active carbon filter is communicated with the water outlet of the candle filter, and a water outlet of the active carbon filter is communicated with the water tank portion.

7. The urea preparation machine as claimed in claim 1, wherein the filtering portion further comprises:
a first water pump, provided on a pipe between the stirring tank and the water tank portion.

8. The urea preparation machine as claimed in claim 7, wherein the filtering portion comprises:
a film filtering portion, wherein the film filtering portion is provided on a pipe between the stirring tank and the water tank portion and positioned above the first water pump.

9. The urea preparation machine as claimed in claim 1, wherein the water tank portion comprises:
a middle water tank, provided above the stirring tank, wherein a water inlet of the middle water tank is communicated with the water outlet of the filtering portion, and a water outlet of the middle water tank is communicated with the heating portion.

10. The urea preparation machine as claimed in claim 9, wherein the water tank portion further comprises:
a pure water tank, provided above the filtering portion and provided parallel to the middle water tank, wherein a water inlet of the pure water tank is communicated with the water outlet of the middle water tank, and a water outlet of the pure water tank is communicated with the heating portion.

11. The urea preparation machine as claimed in claim 9, wherein the filtering portion comprises:
a second water pump provided on a bottom of the cabinet, wherein the second water pump is provided on a pipe connected between the middle water tank and the stirring tank.

12. The urea preparation machine as claimed in claim 1, wherein the material absorbing device comprises:
a housing, wherein a first end of the housing is provided with a feed port, a second end of the housing is provided with a discharge port, the housing is further provided with an exhaust port, the exhaust port is used for exhausting air in the housing, and the feed port forms the material absorbing port.

13. The urea preparation machine as claimed in claim 12, wherein the material absorbing device further comprises:
a separating plate, wherein the separating plate is provided in the housing, an air inlet passage and an air exhaust passage are respectively formed between the separating plate and a side wall of the housing, the exhaust port is communicated with the air exhaust passage, and a flow passing port communicated with the air inlet passage and the air exhaust passage is formed between a bottom of the separating plate and the side wall of the housing.

14. The urea preparation machine as claimed in claim 13, wherein the separating plate comprises:

a first plate section, wherein the first plate section is provided along a vertical direction, a first end of the first plate section is connected with the housing, the feed port and the exhaust port are positioned at two opposite sides of the first plate section; and
a second plate section, wherein the second plate section is connected with a second end of the first plate section and there is an included angle between the second plate section and the second end of the first plate section, and the second plate section is provided away from the exhaust port.

15. The urea preparation machine as claimed in claim 14, wherein the included angle between the second plate section and the second end of the first plate section is a right angle.

16. The urea preparation machine as claimed in claim 12, wherein the material absorbing device comprises:
a suction portion, wherein the suction portion is provided with a suction port and an export, the export is communicated with the feed port, and the suction port forms the material absorbing port.

17. The urea preparation machine as claimed in claim 12, wherein there are a plurality of material absorbing devices, the discharge port of each of the plurality of absorbing devices is communicated with the cavity of the stirring tank, a feed port of one material absorbing device in two neighboring material absorbing devices is communicated with an exhaust port of the other material absorbing device in the two neighboring material absorbing devices.

18. The urea preparation machine as claimed in claim 1, wherein the heating portion comprises a heating water tank, wherein the heating water tank is used for storing and heating water from the water tank portion.

19. A urea preparation machine, comprising:
a cabinet;
a stirring tank, provided in the cabinet;
a filtering portion, provided in the cabinet;
a water tank portion, wherein an inlet of the water tank portion is communicated with an outlet of the filtering portion;
and a heating portion, provided in the cabinet, wherein the heating portion is communicated with an outlet of the water tank portion, and an outlet of the heating portion is communicated with the stirring tank;
wherein the water tank portion comprises:
a middle water tank, provided above the stirring tank, wherein a water inlet of the middle water tank is communicated with the water outlet of the filtering portion, and a water outlet of the middle water tank is communicated with the heating portion; and
a pure water tank, provided above the filtering portion and provided parallel to the middle water tank, wherein a water inlet of the pure water tank is communicated with the water outlet of the middle water tank, and a water outlet of the pure water tank is communicated with the heating portion.

* * * * *